United States Patent
Wang et al.

[11] Patent Number: 6,138,082
[45] Date of Patent: Oct. 24, 2000

[54] STANDARDIZING BETWEEN ANALYTICAL INSTRUMENTS

[75] Inventors: Yongdong Wang, Wilton; Alan M. Ganz, Scarsdale; David H. Tracy, Norwalk; David A. Huppler, Madison; John P. Coates, Newtown, all of Conn.

[73] Assignee: The Perkin Elmer Corporation, Norwalk, Conn.

[21] Appl. No.: 08/993,483

[22] Filed: Dec. 18, 1997

(Under 37 CFR 1.47)

Related U.S. Application Data

[60] Provisional application No. 60/033,726, Dec. 20, 1996.

[51] Int. Cl.$^7$ .................................................. G01R 35/00
[52] U.S. Cl. ............................. 702/109; 702/23; 702/27; 356/319; 356/325; 356/328
[58] Field of Search .............................. 702/109, 22, 23, 702/27, 30, 85, 172; 356/319, 325, 328

[56] References Cited

U.S. PATENT DOCUMENTS

| | | | |
|---|---|---|---|
| 4,866,644 | 9/1989 | Shenk et al. | 364/571.02 |
| 5,303,165 | 4/1994 | Ganz et al. | 356/319 |
| 5,545,895 | 8/1996 | Wright et al. | 702/23 |
| 5,710,713 | 1/1998 | Wright et al. | 702/23 |

FOREIGN PATENT DOCUMENTS 9408225  4/1994  WIPO.

OTHER PUBLICATIONS

Yongdong Wang et al: "Multivariate Instrument Standardization"—Analytical Chemistry, vol. 63, No. 23, Dec. 1991, pp. 2750–2756.

*Primary Examiner*—Marc S. Hoff
*Assistant Examiner*—Hien Vo
*Attorney, Agent, or Firm*—St. Onge Steward Johnston & Reens LLC

[57] ABSTRACT

For conversion of spectral information of an FTIR spectrometric instrument for comparison with that of a dispersion instrument, a first standard function is selected for spectral line shape for the first instrument, and a second standard function for line shape is selected for the second instrument. A conversion factor is computed for converting the first standard function to the second standard function. In ordinary operations, first spectral information is obtained with the first instrument for a first sample, and second spectral information is obtained with the second instrument for a second sample. The conversion factor is applied to the first spectral information to effect converted information, and the converted information is compared with the second spectral information. Such conversion also is applied between chromatographic instruments.

33 Claims, 7 Drawing Sheets

STANDARDIZING BETWEEN ANALYTICAL INSTRUMENTS

This application claims benefit of Provisional application Ser. No. 60/033,726 filed Dec. 20, 1996.

This invention relates to analytical instruments such as spectrometric instruments, and particularly to the conversion of analytical information between such instruments.

BACKGROUND

Analytical instruments are used for a variety of applications generally associated with analyses of materials. One class of such instruments consists of spectrometric instruments, in which a spectrum is generated in interaction with a sample material to effect a spectral beam that is characteristic of the sample and impinged on a photodetector. Modern instruments include a computer that is receptive of spectral data from the detector to generate and compare spectral information associated with the materials. In one type of spectrometric instrument, the spectrum is generated by a dispersion element such as a prism or a holographic grating that spectrally disperses light passed or emitted by a sample or received from a plasma or other excitation source containing sample material. Another type incorporates a time varying optical interference system, in which an interference pattern of light is produced and passed through a sample material that modifies the pattern. Fourier transform computations are applied to the detector signals to transform the modified light pattern into spectral data. The Fourier transform instrument is generally operated in the infrared range, and is known as an "FTIR" instrument.

With improvements in optics, detectors and computerization, there has evolved an ability to perform very precise measurements. Examples are an absorption spectrophotometer, a polychromator or an FTIR instrument that use chemometric mathematical analysis to measure octane number in gasolines. Differences in octane number are associated with subtle differences in near infrared (IR) absorption spectra. The very small changes in spectral characteristics cannot effectively be detected directly by personnel, and computerized automation is a necessity. It also is desirable for such spectral measurements to be effected continuously on-line, typically with an absorption spectrophotometer, whereas an FTIR instrument is often considered a laboratory instrument. Thus there is an interest in utilizing advanced spectrometry methods for analytical chemistry and, more particularly, for precision comparison of information from one type of instrument to that of another.

One aspect of the comparison is that the instruments have intrinsic characteristics that are associated with spectral profiles. Such characteristics are individual to each instrument and may vary with time. Intrinsic characteristics of the instrument distort the data, rendering comparisons inaccurate. In an instrument such as a polychromator with a dispersion grating, an intrinsic characteristic is typified by the profile of spectral data representing a very narrow, sharp spectral line. Such a profile has an intrinsic shape and line width wider than the actual line, due to the fundamental optical design as well as diffraction effects and other imperfections in the optics and (to a lesser extent) electronics in the instrument. An actual intrinsic profile may not be symmetrical. In a polychromator and similar instruments, the instrument profile from a narrow line source is similar to a gaussian profile. For other instruments such as FTIR the intrinsic profile at the limit of interferometer resolution is more rectangular.

U.S. Pat. No. 5,303,165 (Ganz et al), commonly owned by the present assignee, discloses a method and apparatus for standardizing a spectrometric instrument having a characteristic intrinsic profile of spectral line shape for a hypothetically thin spectral line in a selected spectral range. Standardized data is substantially the same as that obtained from the same sample material with any similar instrument, and repeatedly with the same instrument over time.

Conventional FTIR instruments are taught in textbooks such as "Fourier Transform Infrared Spectrometry" by P. R. Griffiths and J. A. de Haseth. In these instruments, an interference pattern of light is produced with a Michaelson or similar interferometer comprising a beam splitter which is a partial reflector that splits white light into two beams. These beams are reflected back and recombined at the beam splitter. The path length of one of the beams is varied with time to produce a time-varied interference pattern. This light pattern is directed through a sample material that modifies the pattern. Fourier transform computations transform the modified pattern into spectral data representing intensity vs. wavenumber.

Other classes of analytical instruments are for chromatography, of which there are two common classes, namely gas chromatography (GC) and liquid chromatography (LC). Gas chromatography, for example as illustrated in U.S. Pat. No. 5,545,252 and U.S. Provisional Patent Application No. 60/006,017 is essentially a physical method of separation in which constituents of a test sample in a carrier gas are adsorbed and desorbed by a stationary phase material in a column. A pulse of the sample is injected into a steady flow of carrier gas. At the end of the column the individual components are separated by time in varying degrees. Detection of a gas property such as thermal conductivity provides a time-scaled pattern which, by calibration or comparison with known samples, indicates the constituents of the test sample qualitatively and quantitatively. The main components of such a system are the column, an injector with a mixing chamber for introducing the sample into the carrier gas, a gas-property detector at the outer end of the column, gas controls and a computer for treating and displaying the output of the detector. Comparisons are of interest between GC instruments having different types of columns or different operating conditions.

Liquid chromatography is similar, for example as illustrated in U.S. Pat. No. 4,886,356 (Paradis) and U.S. Pat. No. 5,173,742 (Young). A pulse of sample is injected into a steady flow of a carrier liquid which is passed through a column and thence through a cell (or two cells) with windows. A light beam is passed through each cell to a photodetector that generates an output signal to a computer, the signal varying with time according to the sample constituents. As with gas chromatography, by computer treatment and calibration or comparison with known samples, the constituents of the test sample may be indicated. Comparisons are of interest between LC instruments having different types of columns or different operating conditions.

Objects of the invention are to provide a novel method and a novel means for transforming analytical information of one of analytical instrument for comparison with spectral information of another type of spectrometric instrument, where the instruments may be different types within the same class of instrument or the same type with different operating conditions. Such objects include providing a novel method and a novel means for transforming spectral information of one spectrometric instrument for comparison with spectral information of another spectrometric instrument. Particular objects are to provide a method and a means for transforming spectral information of an FTIR type of spectrometric instrument for comparison with spectral information of a dispersion type of spectrometric instrument, more particularly where the spectral information of the dispersion type of spectrometric instrument is standardized. Further objects are to provide a novel method and a novel means for transforming analytical information of one chromatographic instrument for comparison with spectral information of another chromatographic instrument of the same class as the first, viz. GC or LC.

SUMMARY OF THE INVENTION

The foregoing and other objects are achieved, at least in part, by a method and, alternatively, by an apparatus for converting spectral information of a first spectrometric instrument for comparison with spectral information of a second spectrometric instrument. In either case, a first standard function is selected for spectral line shape for the first spectrometric instrument, and a second standard function for spectral line shape is selected for the second spectrometric instrument. Preferably each standard function is selected as generally representative of a corresponding intrinsic instrument profile for a hypothetically thin spectral line source. A conversion factor is computed for converting the first standard function to the second standard function.

In ordinary operations, first spectral information is obtained with the first spectrometric instrument for a first sample, and second spectral information is obtained with the second spectrometric instrument for a second sample (which may be the same as or similar to the first sample). The conversion factor is applied to the first spectral information to effect converted information, and the converted information is compared with the second spectral information.

In an advantageous aspect, the first spectrometric instrument comprises an interference FTIR instrument, and the second spectrometric instrument comprises a dispersion instrument. In such situation, the first standard function should be a modified rectangle function, and the second standard function should be a gaussian function, each such function being generally representative of a corresponding intrinsic instrument profile for a hypothetically thin spectral line source. With an instrument such as an FTIR, the first standard function may depend on wavenumber, in which case the conversion factor should comprise a series of sub-factors at selected increments across the spectral range, whereby the sub-factors are dependent on wavenumber.

Objects are achieved, more broadly, by a method or apparatus for converting analytical information of a first analytical instrument for comparison with analytical information of a second analytical instrument. The instrument may be spectrometric (as set forth above), chromatographic (gas or liquid), or other such instrument that effects an analytical profile. A first standard function of analytical profile is selected for the first instrument, a second standard function of analytical profile is selected for the second instrument, and a conversion factor is computed for converting the first standard function to the second standard function. First analytical information is obtained with the first spectrometric instrument for a first sample, and second analytical information is obtained with the second spectrometric instrument for a second sample. The conversion factor is applied to the first analytical information to effect converted information, and the converted information is compared with the second analytical information.

Objects also are achieved with a computer readable storage medium (such as a disk) with appropriate data codes and program codes for use with computers of existing instruments, to effect the conversions set forth herein.

DETAILED DESCRIPTION

In one embodiment, the invention is directed to comparison of spectral output information of two different spectrometric instruments operated in the same selected spectral range. One such instrument (FIG. 1) is, for example, a conventional dispersion instrument of the type disclosed in the aforementioned U.S. Pat. No. 5,303,165 incorporated herein by reference. Such an instrument 10 has a photodetector 11 for which standardization and wavelength calibration is effected. Such an instrument may be, for example, an on-line chemometric spectrographic polychromator requiring high sensitivity and stability in the near infrared for measuring octane number of gasoline. A stable but otherwise ordinary incandescent light source 12 provides light 13 that passes through a relay lens 14 focused on an input end of an optical fiber 16. The fiber directs the light to a probe assembly 18 immersed in a liquid such as the gasoline to be tested. Although shown as a straight-through probe, the probe instead may have folding optics with reflections to lead light back into a return fiber.

Figure 1:
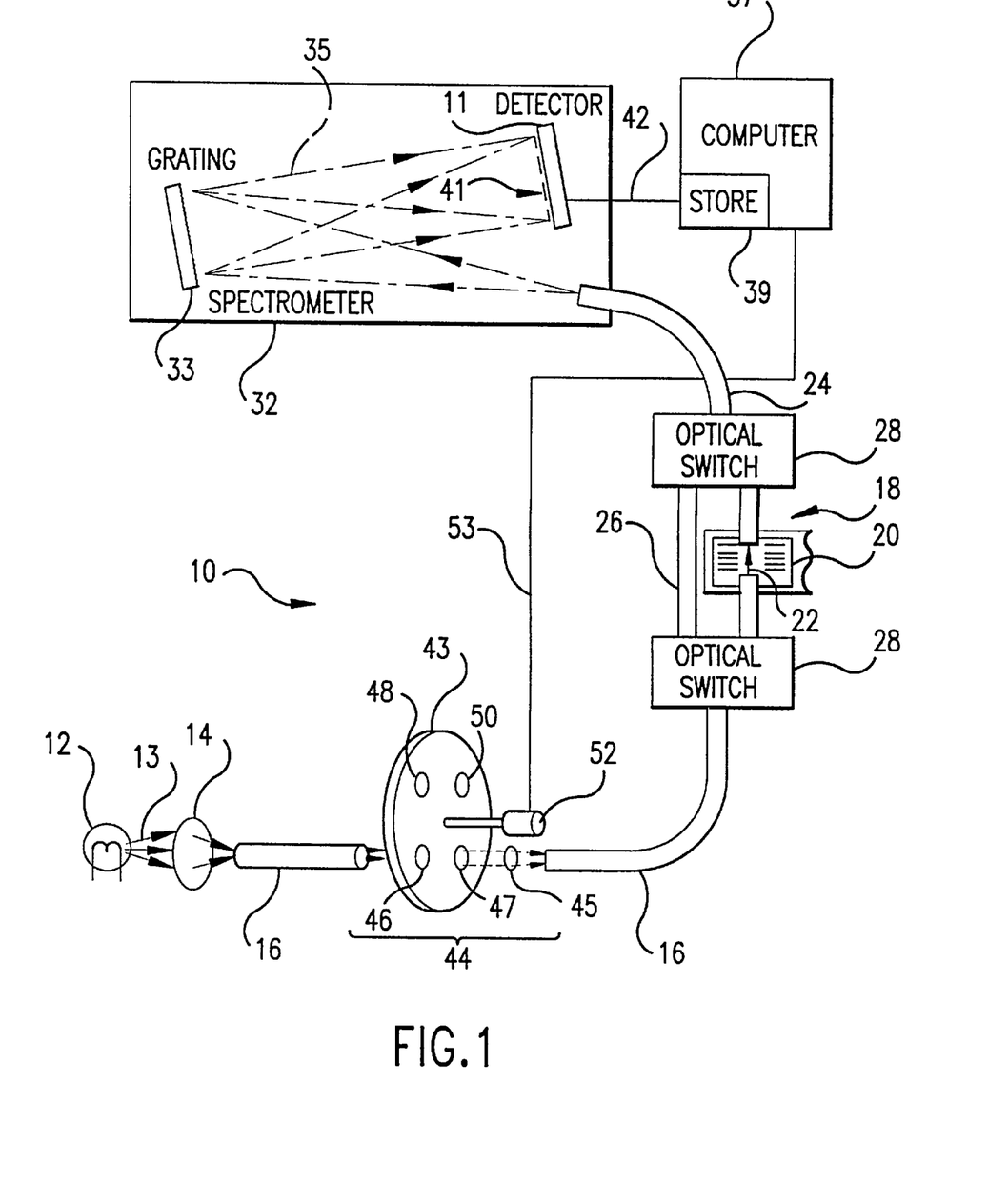
FIG. 1 is a schematic drawing of a dispersion spectrometer as an example of one type spectrometric instrument utilized in the invention.

In the probe a sample space 20 is provided for the liquid so that the light 22 is passed through the liquid, where some of the light may be filtered selectively. The filtered light is picked up by a second optical fiber 24. A bypass fiber 26 with optical switching 28 is provided for selectively bypassing the liquid with the light through the fibers, to provide a standard with which to compare the filtered light. The second fiber 24 carries the light to a spectrometer 32 utilizing a concave holographic grating 33, which disperses the light 35 to the detector 11. Signals from the detector representing the spectrum are directed into a computer 37 for storing 39 on disk or other memory, and processing.

A collimation zone 44 is provided in one of the fibers for inserting a disk 43 having several openings therein. An associated pair of lenses 45 (one shown) pass collimated light through a selected opening between fiber ends. One opening 47 is left empty for passing unfiltered light for normal operation of the instrument to measure samples or background. The other openings contain optical filter elements 46,48,50 used for calibrating and standardizing. The disk is positionable manually or by motor 52 automatically by computer 37 via line 53 (e.g. at selected intervals for recalibrating) for the selected opening or filter.

The other spectrometric instrument utilized in the invention is generally a different type than the first. In a useful embodiment (FIG. 2), the second is a conventional interference FTIR. In this instrument 110, with an optical train 112 an interference fringe pattern is produced by a conventional Michaelson interferometer 114 which varies the fringe pattern in time by oscillating the path difference between interfering beams. The fringe pattern beam 116 is passed through a lens 123 and an aperture 122, and thence is modified by passage through a sample 118 into a beam 120 to a detector that generates corresponding spectral data. Fourier transform computations are applied by a computer 128 to the data to effect spectral information representing intensity vs. wavenumber, the information being representative of the sample. (Wavenumber, generally used in FTIR, is reciprocal of wavelength and proportional to frequency.)

Figure 2:
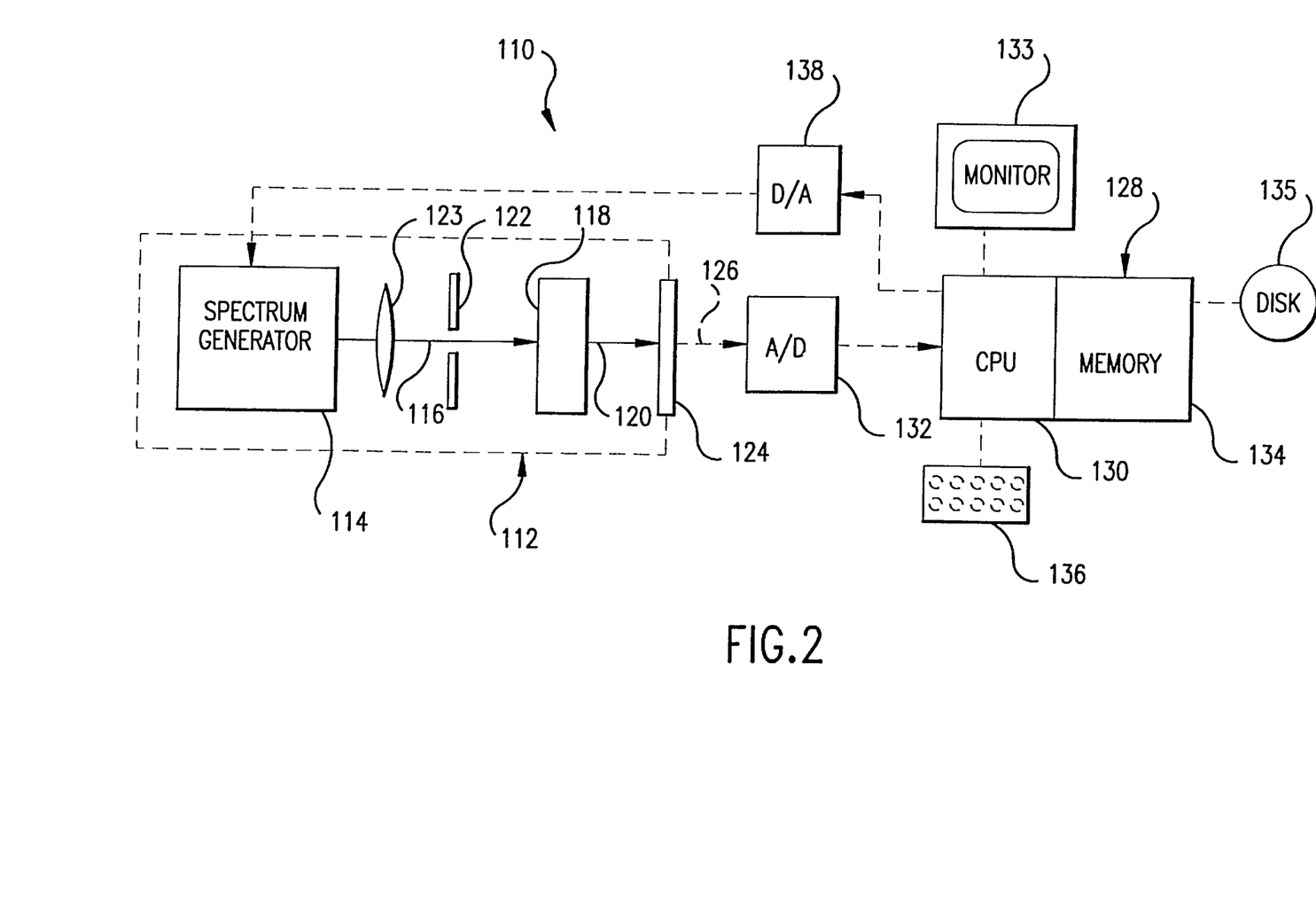
FIG. 2 is a schematic drawing of an FTIR spectrometer as an example of another type spectrometric instrument utilized in the invention.

Computers used with each of the foregoing instruments may be conventional, such as a Digital model DEC PC 590, usually incorporated into the instrument by the manufacturer thereof. The computer, such as the computer 128 of the FTIR, generally includes a central processing unit (CPU) 130 with a analog/digital (A/D) converter 132 receiving signals from the detector 124 on a line 126. Sections of computer memory 134 typically include an internal hard disk and a portable storage medium 135 such as a floppy disk, CD-ROM, and/or a tape with relevant code embedded therein. A keyboard 136 is generally provided for operator input. Spectral information is displayed on a monitor 133 and/or printed. The computer also may provide signals via a digital/analog (D/A) converter 138 to control the interferometer 114. One or more additional dedicated chip processing units may be utilized for certain steps. For example in FTIR, a separate chip is used for the Fourier transform computations, and another for controlling alignment and the like. The present invention is implemented advantageously with the main CPU of a computer associated with at least the first instrument, or the computers of both instruments, utilizing data and program codes representing steps and means for carrying out the invention. Such codes advantageously are provided in a computer-readable storage medium such as the hard disk of the computer or a floppy disk that may be utilized with the computer of an otherwise conventional instrument.

Programming is conventional such as with "C++" which generally is incorporated into the computer by the manufacturer of the computer or the instrument for conventional operations. Adaptations of the programming are made for the present invention. Programming from flow diagrams and descriptions herein is conventional and readily effected by one skilled in the art. The details of such programming are not important to this invention. As the computer computations may involve considerable data and therefore be extensive, a high performance processor such as an Intel Pentium™ of at least 100 MHz is recommended, although a 486 processor should be sufficient.

Each of the foregoing instruments effects spectral information that is imperfect. For a spectral source effecting a very narrow line, the spectral information is line broadened to a profile having a finite width. In the case of a dispersion instrument, the profile may be approximated by a gaussian function with a full width at half the maximum peak height (FWHM) that represents instrument resolution.

In the case of an FTIR instrument the spectral information from a narrow line source may be approximated as a modified rectangle with a width $\delta\sigma$ representing resolution. The rectangle width is determined, for example being approximated theoretically (in a conventional manner) by $$\delta\sigma = \beta^2 \sigma / 8 \qquad \text{Eq. 1}$$

where $\beta B = \sin^{-1}$ (d/f), d is the diameter for an aperture between the interferometer and the sample, and f is the focal length of the lens 123 that images the aperture 122 on the sample (e.g. d=4.2 mm and f=120 mm).

The modification of the rectangle is associated with the Fourier transform of an apodization factor. The intensity associated with any one wavelength in the interference beam from the interferometer is in the form a time-dependent sine wave representing the varying path length. The ends of the sine wave are truncated by the limits of the path change in the interferometer, e.g. the reflector rotation. Since the computer processing treats the waveform as infinite in length, a distortion is introduced by the truncation. For better interpretation, data in current FTIR instruments are treated by multiplying the data vector by a matrix correction factor, known as an "apodization" factor A, representing a weighting function. This factor may be preselected by theoretical considerations as a mathematical function, having a calculated width associated with the cutoff of the ends of a sine wave, known from the cycle limits of the interferometer mirrors. In wavenumber space the modified rectangle function T:

$$T = R * A \qquad \text{Eq. 2}$$

where R is a rectangle function of width $\delta\sigma$ (Eq. 1) that is multiplied by an apodization factor, for example a sinc function $A = \sin(2\pi\sigma L_m)/(2\pi\sigma L_m)$ where $L_m$ is the maximum difference in optical path lengths of the split interfering beams in the interferometer. This modified function is in the form of a central peak with diminishing sinusoidal tails.

(As used herein and in the claims, the term "multiplication" and its corresponding symbol "*" for matrix operations means either direct multiplication or a related procedure such as convolution. Similarly the terms "division", "ratio" and their corresponding symbol "/" for matrix operations means either direct division or a related procedure such as deconvolution.)

In addition to finite widths for narrow line sources, there are intrinsic distortions in the spectral information for each instrument. The distortion is represented in a characteristic intrinsic profile of spectral line shape for a hypothetically thin spectral line source. As disclosed in the aforementioned U.S. Pat. No. 5,303,165, the instrument or its data may be standardized from this distortion by selection of a target profile that is selected for a hypothetically sharp spectral line. The instrument is operated with a narrow line source to produce profile data representative of the intrinsic profile. A transformation filter is computed for transforming the profile data to the target profile. The instrument then is operated normally with a sample source to produce sample data representative of a sample spectrum, and the transformation filter is applied to the sample data to generate the spectral information which is thereby standardized for comparison with similar standardized information from any instrument of the same type.

In FTIR there also is an intrinsic distortion. Its spectral information may be modified by a standardization, for example as disclosed in copending U.S. patent application Ser. No. 08/993,482 filed Dec. 18, 1997 (concurrently herewith) and commonly owned by the present assignee. However, such standardization of this spectral information should not be necessary in view of the present invention, and the information may be utilized directly from the Fourier transform.

Figure 3:
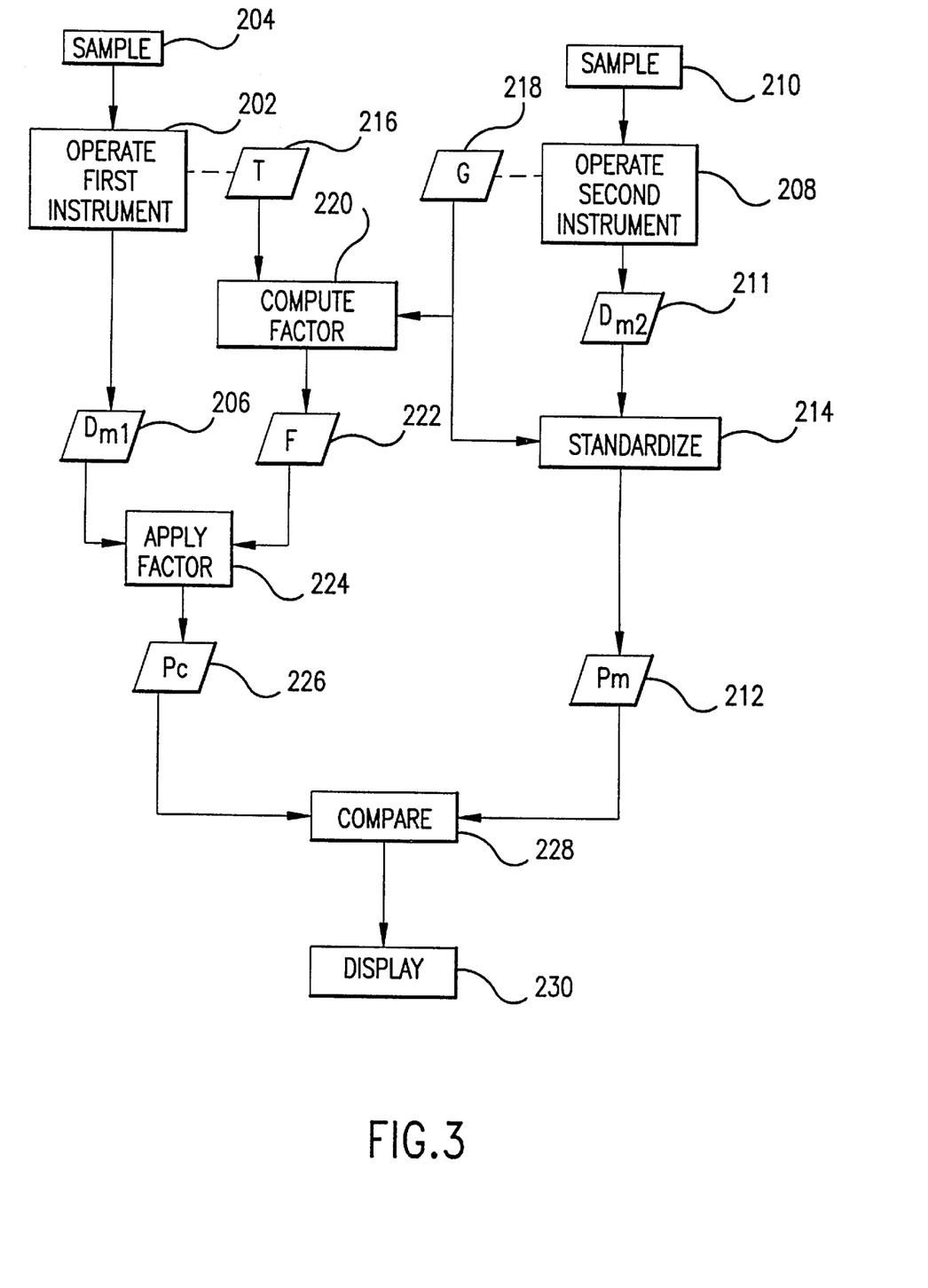
FIG. 3 is a flow chart showing application of the invention with respect to two instruments such as those of FIGS. 1 and 2.

FIG. 3 illustrates a method of and means for applying the invention with the foregoing instruments. Normal operation 202 of the first instrument (e.g. FTIR) with a test sample 204 effects a set 206 of measured spectral data $D_{m1}$, Similarly, normal operation 208 of the second instrument (e.g. dispersion) with the same or another (usually similar) test sample 210 effects another set 211 of spectral data $D_{m2}$. Preferably the data $D_{m2}$ of the second instrument is standardized 214 into a set 212 of spectral information $P_m$, in the manner of the aforementioned U.S. Pat. No. 5,303,165 as summarized above. The corresponding data 206 for the first instrument may, but (as shown) need not be so standardized.

Generally prior to these operations of the instruments, a first standard function T is selected 216 for spectral line shape for the first spectrometric instrument. This should be an idealized profile, such as the above-mentioned modified rectangle function for the FTIR. The profile should be generally representative of a corresponding intrinsic profile for a hypothetically thin spectral line source. (The term "generally representative" in the present context means that the function need only approximate the intrinsic profile, advantageously using a mathematically convenient function.) If the data of the first instrument is standardized, the ideal function or target profile of the standardization preferably is selected. If the data is not standardized, the function of Eq. 2 is suitable for the present case of FTIR being the first instrument.

A second standard function G, different than the first standard function T, also is selected 218 for spectral line shape for the second spectrometric instrument. This also should be an idealized profile, such as a gaussian function for a dispersion instrument. This also preferably is generally representative of a corresponding intrinsic instrument profile for a hypothetically thin spectral line source. Preferably the standard function G is the same as that selected for the target profile utilized in standardizing 214 the second spectrometric information $P_m$.

A conversion factor F is computed 220 for converting the first standard function to the second standard function, using a relationship $$G = T*F \qquad \text{Eq. 3}$$

where F is the conversion factor being computed, T is the first standard function (e.g. modified rectangle) and G is the second standard function (e.g. gaussian). For computer operations, the standard functions and the spectral information are represented as vectors defined by stored data for selected intervals across the selected spectral range. The conversion factor F is thus in the form of a matrix (or a series of matrices as explained below), with its data being stored 222 permanently on disk for routine use on spectral information.

Conversion of units should be included as necessary in the relationship defining the conversion F. Thus the factor F preferably includes a conversion to the units of the second instrument. For example if FTIR data are usually in terms of wavenumber (cm$^{-1}$), and dispersion instrument data are in terms of wavelength, wavenumber should be converted to wavelength. Also, the standard functions each should be normalized to unit area. As referenced herein and in the claims, the relationship as represented by Eq. 3 includes such modifications as unit conversion and normalization.

Measured spectral information $D_{m1}$ is obtained for the first instrument (e.g. FTIR), and measured and standardized second spectral information $P_m$ is obtained for the second instrument (e.g. dispersion). The conversion factor F is applied 224 by multiplication with the first spectral information $D_{m1}$ to compute converted information $P_c$ from the relationship:

$$P_c = D_{m1}*F \qquad \text{Eq. 4}$$

The converted information $P_c$ is saved 226 and compared 228 with the measured spectral information $P_m$. Such comparison may be made visually or by computer which, for example, may calculate and display 230 the difference $P_m - P_c$ for each wavelength increment.

Figure 4:
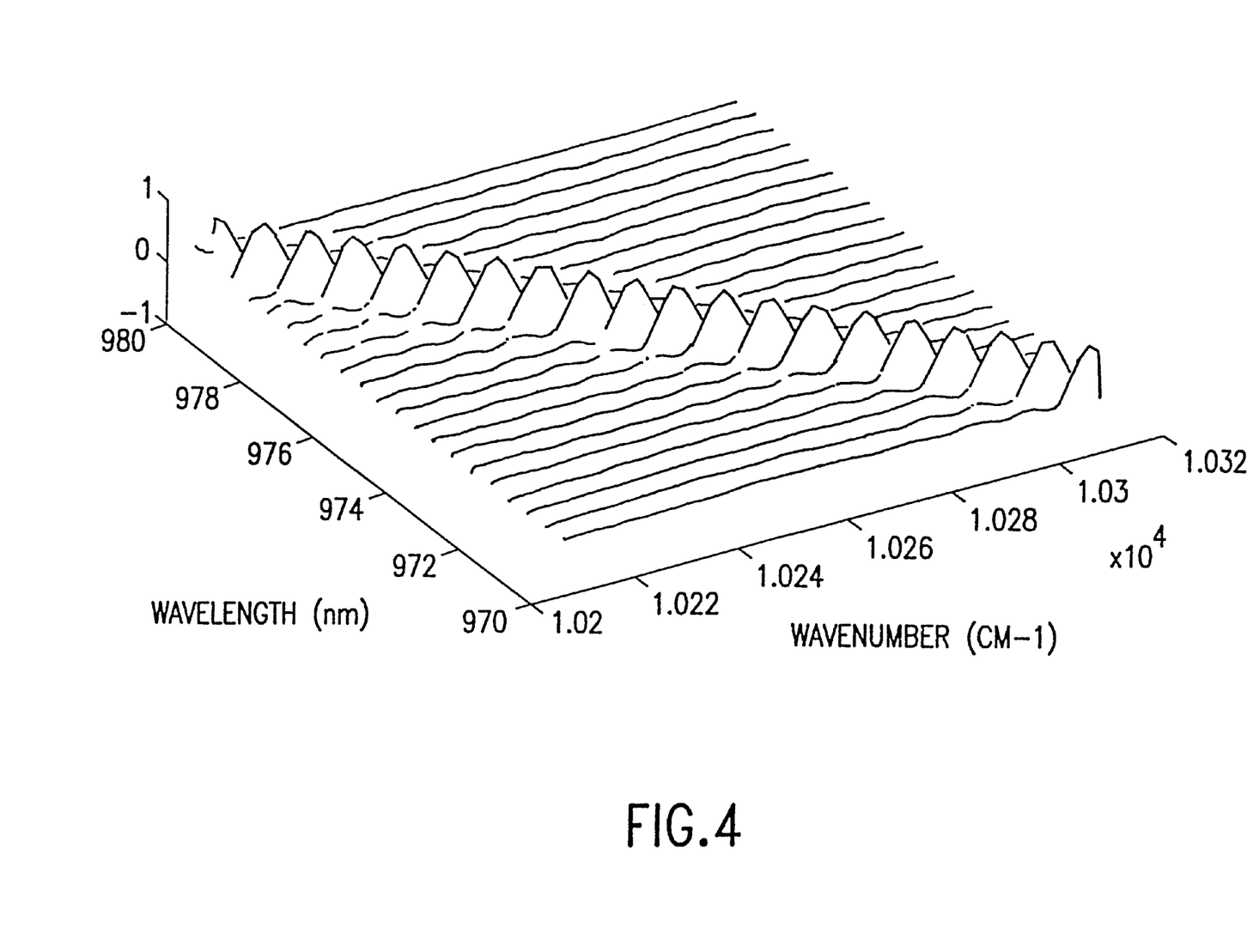
FIG. 4 illustrates a series of sub-functions computed with reference to the flow chart of FIG. 3.

As indicated by Eq. 1, a characteristic of FTIR is that the limit of resolution $\delta\sigma$ (minimum line width) attributable to the aperture is a function of the spectral wavenumber, in particular being proportional to the wavenumber with greater line width at higher wavenumber. This results in the first standard function T being dependent on wavenumber. (The second standard function, viz. gaussian, may but need not be independent of wavenumber.) Such dependence is treated by selecting a standard sub-function $T_i$ at each selected wavenumber increment i across the spectral range. The increments should be selected to correspond to those used for the second instrument; for example in an operational wavelength range of 800 to 1100 nm, at 0.5 nm intervals there are 601 points. The function range should be extended, for example by 5 nm, at each end to handle the computations for the actual range. FIG. 4 illustrates a series of sub-functions $T_i$, each being a function of wavenumber for a wavelength increment. Selection of the first standard function T thus comprises selection of the series of sub-functions $T_i$.

Figure 5:
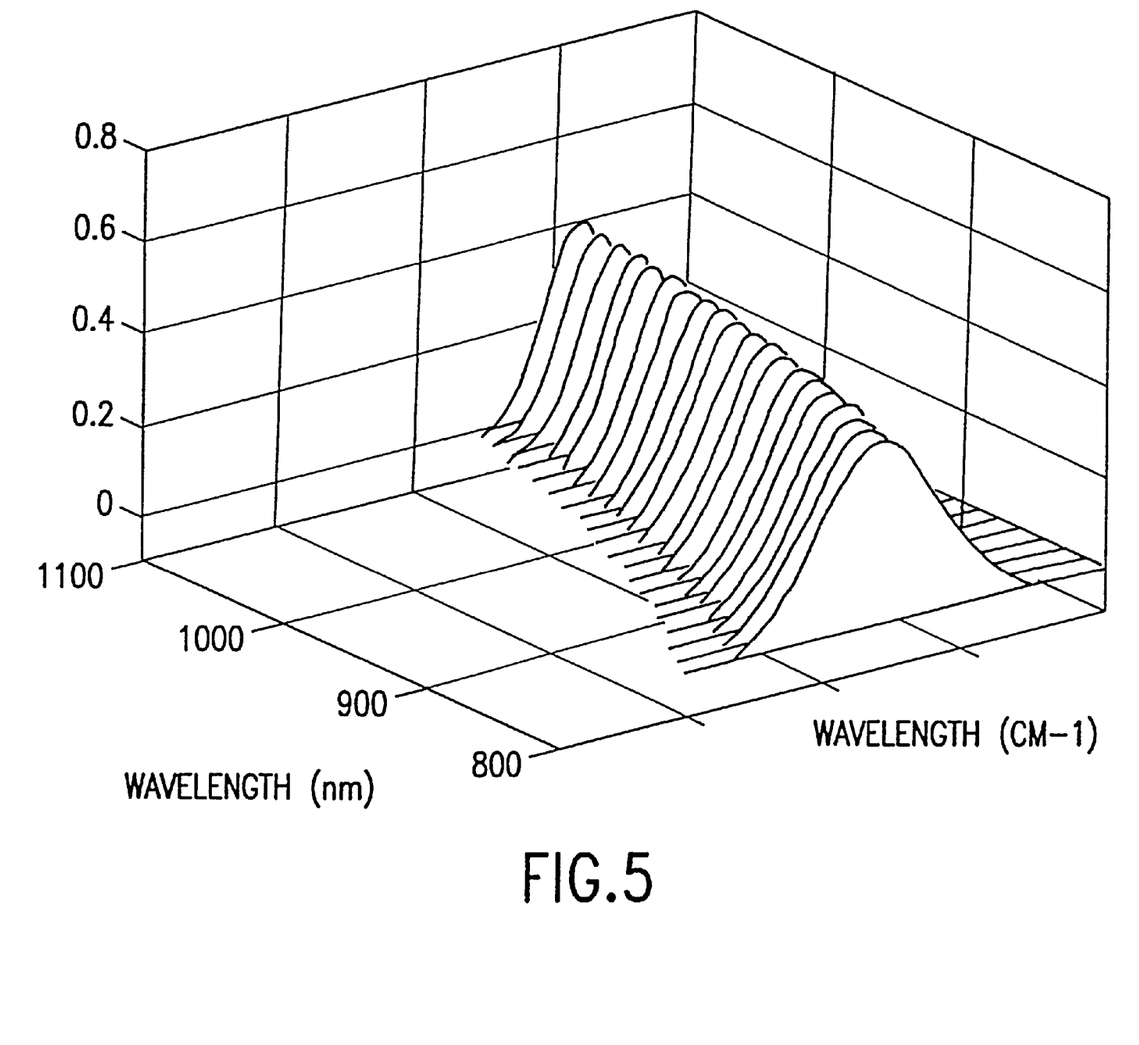
FIG. 5 illustrates a series of sub-factors computed from the sub-functions of FIG. 4.

To effect computation of the factor F, a sub-factor $F_i$ is computed for each sub-function $T_i$ using the second function G (which in this embodiment is independent of wavelength), by $G = T_i * F_i$ from Eq. 3, resulting in a series of sub-factors $F_i$ that define the conversion factor F. A set of sub-factors is illustrated in FIG. 5. (The wavenumber axes for successive wavelengths are shifted to more readily show the sub-factors in a graph; actually the successive sub-factors are offset more than the sub-functions of FIG. 4.) This series of computations is lengthy, for example taking 2.5 hours with a Gateway™ 486-50 computer. However, this only needs to be done once and stored for each pair of instrument types. This stored data is not sensitive to individual instruments, and thus may be utilized generally. Wavenumber increments should correspond to selected increments for the dispersion instrument which, for example, are desirably two points per resolution; e.g. 0.5 cm$^{-1}$ for a resolution of 1.0 cm$^{-1}$.

The sub-factor matrices $F_i$ are applied to ordinary spectral information obtained from normal operation of the first (FTIR) instrument, to effect converted spectral information. To do this, each matrix $F_i$ is multiplied by spectral data around the corresponding wavenumber i. The sub-factors should be applied to several points around each , e.g. ±5 points (total of 11 points) around each wavenumber increment. The sub-factors are relatively simple, and the conversion convolution computations can be done quickly, for example in 1 to 2 seconds with the conventional sparse matrix method using a Gateway™ 486-50 computer.

Accurate wavenumber calibration of the first (FTIR) instrument should be effected for precision comparison with standardized spectral information of the second instrument. This can be done conventionally with standard samples, and should be done periodically (e.g. weekly or monthly),with the instrument in use.

The foregoing is described particularly with respect to converting non-standardized spectral information of an interference FTIR spectrometer for comparison with standardized spectral information of a dispersion spectrometer. More generally, use of these instruments illustrates conversion of higher resolution data for comparison with lower resolution data and, also, conversion from a non-standardized instrument to a standardized instrument. Both of these types of conversions are advantageous.

The FTIR may be used as a laboratory instrument for which comparisons are made with an on-line dispersion spectrometer used in production. Selection of this pair of instruments is especially suited for application of this invention. However, there is no such restriction in application of the invention. For example, as indicated above, the FTIR spectral information may be standardized, or neither instrument may have standardization. The spectrometers of the present example operate in the infra-red (IR) range, but the other spectral ranges visible and ultraviolet are applicable. Other spectrometers that may utilize the invention include atomic emission spectrophotometers such as the induction plasma type, atomic absorption spectrometers, fluorescence instruments, Raman instruments and optical filter instruments. Any of these or other desired spectrometric instruments may be used and paired according to the present invention. In the present example, the resolution and conversion for the FTIR instrument are dependent on wavenumber; however, more generally, either or both or neither instrument may depend on wavenumber.

The invention may also be utilized to convert in circumstances where the first and second types of instruments are substantially the same type, such as both FTIR or both grating type. One advantage of this is to select the second instrument as a standard where the first instrument may actually differ from instrument to instrument, so that the selected functions may be different. Another advantage is specific to FTIR (or other) instruments, wherein the resolution varies with (e.g. is proportional to) wavelength, in that the converted data can have a resolution that is independent of wavelength. In a further aspect, the second instrument may be hypothetical and not particularly related to any specific instrument or even to any particular type of instrument. In this case spectral data of one or more types of first instruments could be converted into a common data type for general comparisons.

In a further embodiment, it also is useful to provide the means for instrument users to effect the foregoing conversions in a manner illustrated in FIG. 3, with a computer readable storage medium such as a floppy disk, CD-ROM or tape. The storage medium has data code and program code embedded therein so as to be readable by the computing means. The data code includes the conversion factor 222 precomputed from the first standard function 216 and the second standard function 218 of preselected types of instruments. The program code includes means for applying 224 the conversion factor to first spectral information 206 to effect converted information 226 for the comparison. The program code may simply result in a display of the converted information for the comparison, or may further comprise the means for comparing 228 the converted information 226 with the second spectral information 212. More detailed aspects of this embodiment are as described above.

Although described above for comparing spectral data of different types of instruments, the invention may be applied to compare spectral data of the same type of instrument, e.g. either a dispersion type or an FTIR type, wherein the instruments differ in operating conditions or by different models. For example in FTIR, one instrument may have four wave number resolution or eight wave number resolution.

Figure 6:
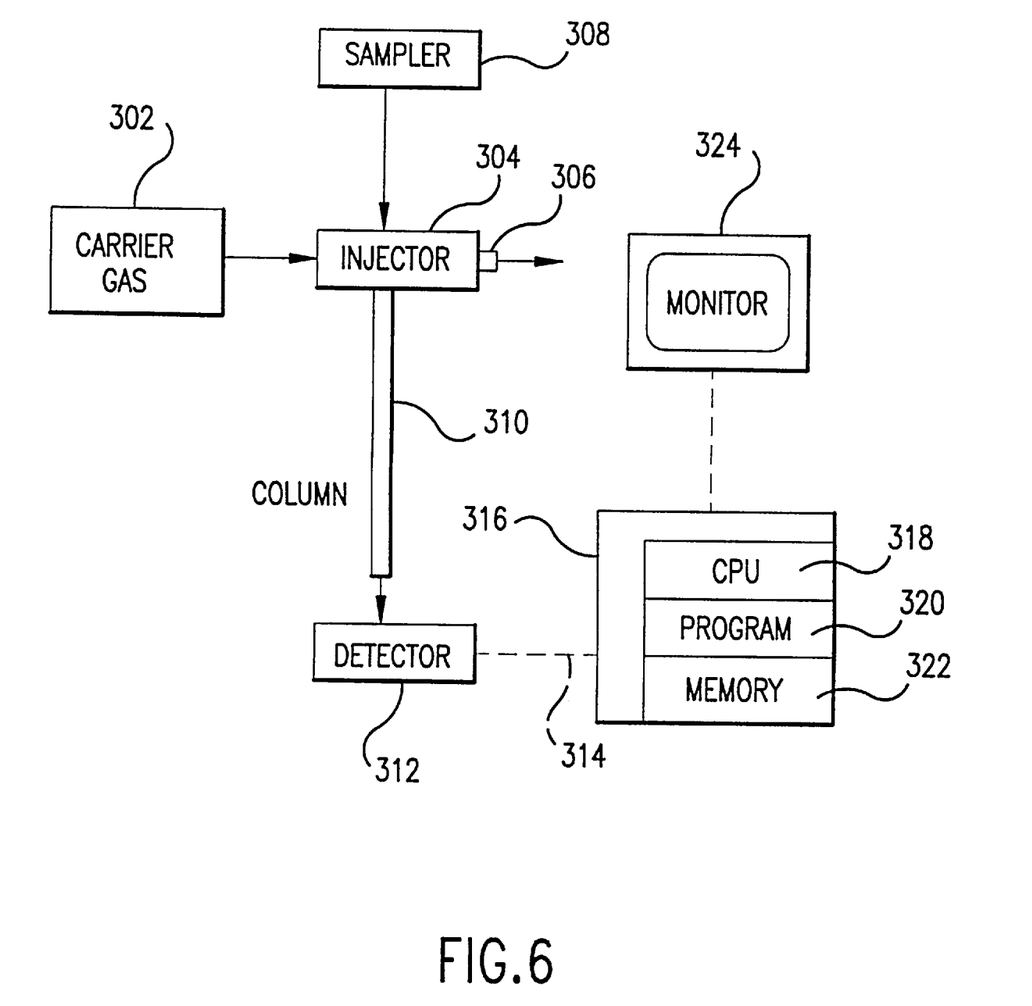
FIG. 6 is a schematic drawing of a gas chromatograph as an example of a type of analytic instrument utilized in the invention.

The invention also may be applied to other classes of analytical instruments such as gas chromatographs (GC) where the instruments differ in style, column characteristics and/or operating conditions. Examples of different style instruments are disclosed in the aforementioned U.S. Pat. No. 5,545,252 and Provisional Patent Application No. 60/006,017 (both Hinshaw, of the present assignee) which differ in carrier gas flow control as well as sample transfer method, and are incorporated herein by reference to illustrate such instruments and their operation. A "generic" GC is shown schematically in FIG. 6. A carrier gas is conveyed from a source 302 thereof to an injector 304, and some or a majority of this gas may exit from a port 306 in the injector (with selected backpressure, not shown). Sample 308 is introduced momentarily into the injector where it is entrained into the carrier gas. At least a portion of the resulting mixture is passed from the injector through the column 310 which adsorbs and elutes components of the sample at different rates. The carrier gas mixture exiting the column passes through a detector 312 which measures changes with time in a physical characteristic of the gas such as thermal conductivity. A detector signal is conveyed on a line 314 to a computer 316 with a CPU 318, program 320 and memory 322 for analysis into an output pattern of analytical information which may be displayed on a monitor 324.

The analytical information from two different GC instruments (such as disclosed in the two Hinshaw patents, or with different columns or operating conditions), may be compared in the manner described above with respect to FIG. 3. In the case of GC, the line shapes or profiles leading to the standard functions T and G are elution profiles. Preferably each of these functions generally is representative of a corresponding intrinsic instrument elution profile for a hypothetical, instantaneously brief introduction of sample (analogous to the hypothetically thin spectral line for a spectrometer). Such profile may be defined with an exponentially modified gaussian function such as disclosed in an article "Robust Method for Qualitative Analysis of Two-Dimensional (Chromatographic/Spectral) Data Sets" by D. H. Burns, J. B. Callis and G. D. Christian, Anal. Chem. 58, 1475–1420 (1986). As for the spectrometers, appropriate data and program codes may be stored on a disk or other computer readable medium for use with computers of existing chromatographic instruments.

Figure 7:
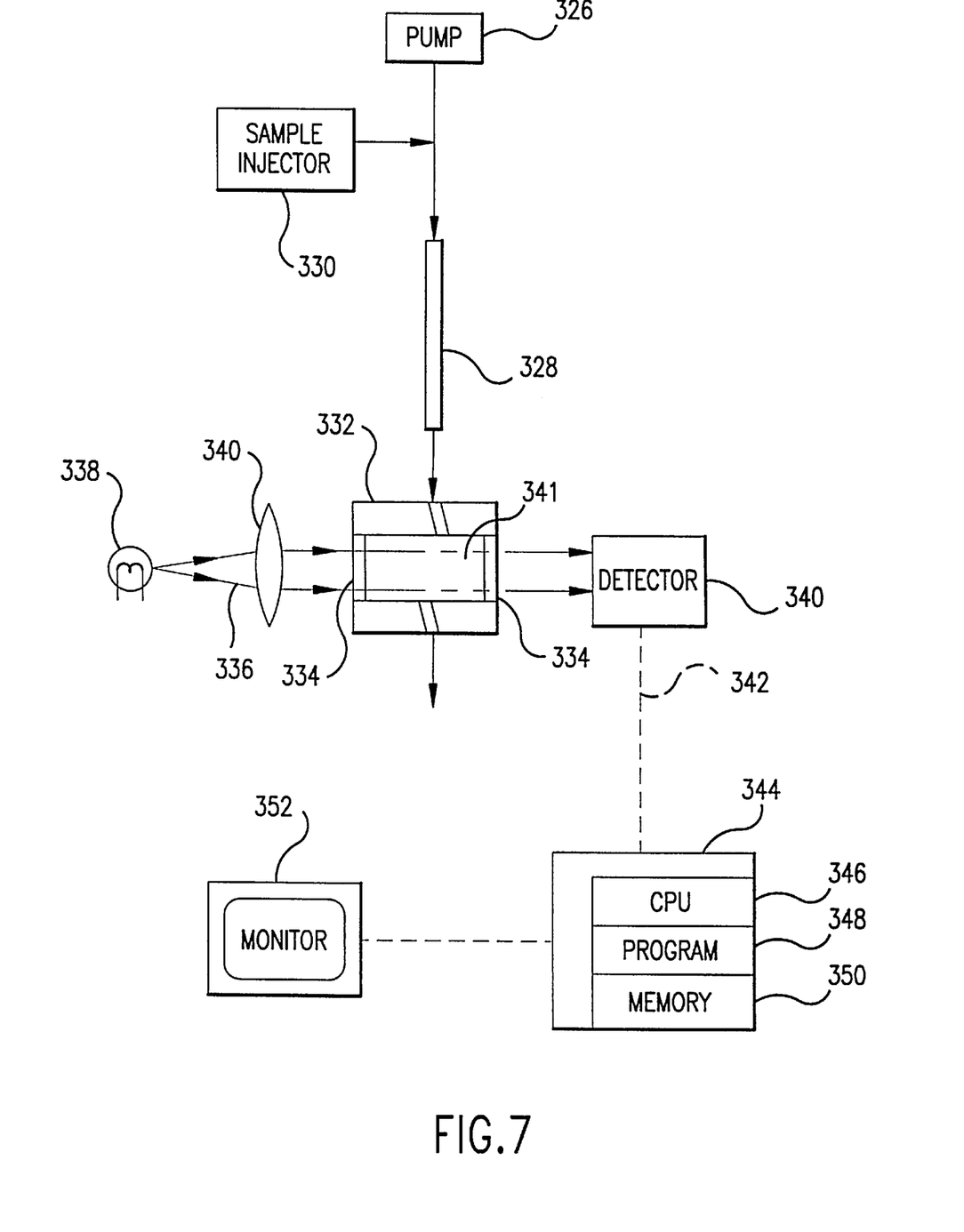
FIG. 7 is a schematic drawing of a liquid chromatograph as an example of another type of analytic instrument utilized in the invention.

The invention may be applied similarly for comparison between different liquid chromatographic instruments, the same instrument with different column or operating conditions, such as those of the aforementioned U.S. Pat. No. 4,886,356 (Paradis) and U.S. Pat. No. 5,173,742 (Young), both incorporated herein by reference. Column characteristics again include dimensions and adsorption agent, and operating conditions include carrier gas type and flow rate, and inlet and outlet pressures. A "generic" LC is shown schematically in FIG. 7. A liquid carrier is conveyed from a pump 326 to a column 328. Sample is introduced momentarily from an injector 330 into the pipe between the pump and the column where it is entrained into the liquid carrier. The resulting mixture is passed through the column which adsorbs and elutes components of the sample at different rates. The mixture exiting the column passes through a cell 332 with windows 334. A beam 336 of light from a light source 338 is collimated by a lens 340 or other suitable optics and passed through the liquid 341 in the cell to a detector 340 which measures changes with time in the mixture as manifested in light absorption. A detector signal is conveyed on a line 342 to a computer 344 with a CPU 346, stored program 348 and memory 350 for analysis into an output pattern which may be displayed on a monitor 352. As with GC, comparisons may be made in the manner described with respect to FIG. 3, using an exponentially modified gaussian function for the standard functions.

Other classes of instruments suitable for the invention are mass spectrometers, analytical x-ray instruments, and other analytical instruments that effect analytical profiles in the analysis of substances.

As used herein and in the claims, the term "analytical profile" includes spectral line shape and similar profiles associated with chromatographs and other analytical instruments that effect such profiles as a function of wavelength, time or the like. Similarly, "analytical information" includes spectral information and similar information associated with chromatographs and such other analytical instruments.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A method for converting analytical information of a first analytical instrument for comparison with analytical information of a second analytical instrument, the method comprising steps of selecting a first standard function of analytical profile for the first instrument, selecting a second standard function of analytical profile for the second instrument, computing a conversion factor for converting the first standard function to the second standard function, obtaining first analytical information with the first instrument for a first sample, obtaining second analytical information with the second instrument for a second sample, applying the conversion factor to the first analytical information to effect converted information, and comparing the converted information with the second analytical information, wherein each standard function is a selected mathematical function generally representative of a corresponding intrinsic instrument profile for a hypothetically thin spectral line source, and the second standard function is different than the first standard function.

2. The method of claim 1 wherein each analytical instrument is a chromatographic instrument.

3. A method for converting spectral information of a first spectrometric instrument for comparison with spectral information of a second spectrometric instrument in a selected spectral range, the method comprising steps of selecting a first standard function for spectral line shape for the first spectrometric instrument, selecting a second standard function for spectral line shape for the second spectrometric instrument, computing a conversion factor for converting the first standard function to the second standard function, obtaining first spectral information with the first spectrometric instrument for a first sample, obtaining second spectral information with the second spectrometric instrument for a second sample, applying the conversion factor to the first spectral information to effect converted information, and comparing the converted information with the second spectral information.

4. The method of claim 3 wherein each standard function is selected as generally representative of a corresponding intrinsic instrument profile for a hypothetically thin spectral line source.

5. The method of claim 3 wherein the first spectrometric instrument comprises an interference FTIR instrument, and the second spectrometric instrument comprises a dispersion instrument.

6. The method of claim 5 wherein the first standard function is a modified rectangle function, and the second standard function is a gaussian function, each such function being generally representative of a corresponding intrinsic instrument profile for a hypothetically thin spectral line source.

7. The method of claim 6 wherein the first standard function is dependent on wavenumber, and the conversion factor comprises a series of sub-factors at selected increments across the spectral range, whereby the sub-factors are dependent on wavenumber.

8. The method of claim 3 wherein the second spectral information is standardized with the second standard function.

9. The method of claim 8 wherein:

each standard function is selected as generally representative of corresponding intrinsic instrument profile for a hypothetically thin spectral line source, the second spectrometric instrument has a characteristic intrinsic profile of spectral line shape with intrinsic width for a hypothetically thin spectral line, and the second spectrometric instrument includes a line source of a narrow spectral line with an associated line width substantially narrower than the intrinsic width;

the method further comprises effecting the standardized second spectral information by steps of initially operating the second spectrometric instrument with the line source to produce profile data for the narrow spectral line such that the profile data is representative of the intrinsic profile, and computing a transformation filter for transforming the profile data to the second standard function; and the step of obtaining second spectral information comprises normally operating the second spectrometric instrument with a sample source to produce sample data representative of a sample spectrum, and applying the transformation filter to the sample data to generate the second spectral information.

10. The method of claim 9 wherein at least one standard function is dependent on wavenumber, and the conversion factor comprises a series of sub-factors at selected increments across the spectral range, whereby the sub-factors are dependent on wavenumber.

11. The method of claim 10 wherein the first spectrometric instrument comprises an interference FTIR instrument, the second spectrometric instrument comprises a dispersion instrument, the first standard function is a modified rectangle function dependent on wavenumber, and the second standard function is a gaussian function.

12. An apparatus for converting analytical information for comparison, comprising a first analytical instrument having a selected first standard function for analytical profile, a second analytical instrument having a selected second standard function for analytical profile, means for computing a conversion factor for converting the first standard function to the second standard function, means for obtaining first analytical information with the first instrument for a first sample, means of obtaining second analytical information with the second instrument for a second sample, means for applying the conversion factor to the first analytical information to effect converted information, and means for comparing the converted information with the second analytical information, wherein each standard function is a selected mathematical function generally representative of a corresponding intrinsic instrument profile for a hypothetically thin spectral line source, and the second standard function is different than the first standard function.

13. The apparatus of claim 12 wherein each analytical instrument is a chromatographic instrument.

14. An apparatus for converting spectral information for comparison in a selected spectral range, comprising a first spectrometric instrument having a selected first standard function for spectral line shape, a second spectrometric instrument having a selected second standard function for spectral line shape, means for computing a conversion factor for converting the first standard function to the second standard function, means for obtaining first spectral information with the first spectrometric instrument for a first sample, means for obtaining second spectral information with the second spectrometric instrument for a second sample, means for applying the conversion factor to the first spectral information to effect converted information, and means for comparing the converted information with the second spectral information.

15. The apparatus of claim 14 wherein each standard function is generally representative of a corresponding intrinsic instrument profile for a hypothetically thin spectral line source.

16. The apparatus of claim 14 wherein the first spectrometric instrument comprises an interference FTIR instrument, and the second spectrometric instrument comprises a dispersion instrument.

17. The apparatus of claim 16 wherein the first standard function is a modified rectangle function, and the second standard function is a gaussian function, each such function being generally representative of a corresponding intrinsic instrument profile for a hypothetically thin spectral line source.

18. The apparatus of claim 17 wherein the first standard function is dependent on wavenumber, and the conversion factor comprises a series of sub-factors at selected increments across the spectral range, whereby the sub-factors are dependent on wavenumber.

19. The apparatus of claim 14 wherein the second spectral information is standardized with the second standard function.

20. The apparatus of claim 19 wherein:
   each standard function is generally representative of corresponding intrinsic instrument profile for a hypothetically thin spectral line source, the second spectrometric instrument has a characteristic intrinsic profile of spectral line shape with intrinsic width for a hypothetically thin spectral line, and the second spectrometric instrument includes a line source of a narrow spectral line with an associated line width substantially narrower than the intrinsic width;
   the apparatus further comprises means for effecting the standardized second spectral information, said means comprising means for initially operating the second spectrometric instrument with the line source to produce profile data for the narrow spectral line such that the profile data is representative of the intrinsic profile, and means for computing a transformation filter for transforming the profile data to the second standard function; and
   the means for obtaining second spectral information comprises means for normally operating the second spectrometric instrument with a sample source to produce sample data representative of a sample spectrum, and means for applying the transformation filter to the sample data to generate the second spectral information.

21. The apparatus of claim 20 wherein at least one standard function is dependent on wavenumber, and the conversion factor comprises a series of sub-factors at selected increments across the spectral range, whereby the sub-factors are dependent on wavenumber.

22. The apparatus of claim 21 wherein the first spectrometric instrument comprises an interference FTIR instrument, the second spectrometric instrument comprises a dispersion instrument, the first standard function is a modified rectangle function dependent on wavenumber, and the second standard function is a gaussian function.

23. A computer readable storage medium for utilization in conversion of analytical information for comparison between first spectral information obtained with a first analytical instrument having a selected first standard function for analytical profile, and second analytical information obtained with a second analytical instrument having a selected second standard function for analytical profile, the storage medium being utilizable with computer means for effecting the conversion, and the storage medium having data code and program code embedded therein so as to be readable by the computing means, the data code comprising a conversion factor for converting the first standard function to the second standard function, and the program code comprising means for applying the conversion factor to the first analytical information to effect converted information for the comparison.

24. The storage medium of claim 23 wherein the analytical instrument is a chromatographic instrument.

25. A computer readable storage medium for utilization in conversion of spectral information for comparison in a selected spectral range, the comparison being between first spectral information obtained with a first spectrometric instrument having a selected first standard function for spectral line shape, and second spectral information obtained with a second spectrometric instrument having a selected second standard function for spectral line shape, the storage medium being utilizable with computer means for effecting the conversion, and the storage medium having data code and program code embedded therein so as to be readable by the computing means, the data code comprising a conversion factor for converting the first standard function to the second standard function, and the program code comprises means for applying the conversion factor to the first spectral information to effect converted information for the comparison.

26. The storage medium of claim 25 wherein the program code further comprises means for comparing the converted information with the second spectral information.

27. The storage medium of claim 25 wherein each standard function is generally representative of a corresponding intrinsic instrument profile for a hypothetically thin spectral line source.

28. The storage medium of claim 25 wherein the first spectrometric instrument comprises an interference FTIR instrument, and the second spectrometric instrument comprises a dispersion instrument.

29. The storage medium of claim 28 wherein the first standard function is a modified rectangle function, and the second standard function is a gaussian function, each such function being generally representative of a corresponding intrinsic instrument profile for a hypothetically thin spectral line source.

30. The storage medium of claim 29 wherein the first standard function is dependent on wavenumber, and the conversion factor comprises a series of sub-factors at selected increments across the spectral range, whereby the sub-factors are dependent on wavenumber.

31. The storage medium of claim 25 wherein the second spectral information is standardized with the second standard function.

32. The method of claim 3 wherein each standard function is a mathematical function.

33. The apparatus of claim 14 wherein each standard function is a mathematical function.

* * * * *